US005995865A

United States Patent [19]
Carioni

[11] Patent Number: 5,995,865
[45] Date of Patent: Nov. 30, 1999

[54] THERMOGRAPHIC DEVICE FOR EXAMINING THE BLOOD CIRCULATION

[75] Inventor: Armando Carioni, Castelletro d'Erro Al, Italy

[73] Assignee: Dalesby Limited, United Kingdom

[21] Appl. No.: 09/120,586

[22] Filed: Jul. 22, 1998

[30] Foreign Application Priority Data

Jun. 17, 1998 [IT] Italy .................................. MI98A1383

[51] Int. Cl.⁶ ...................................................... A61B 5/00
[52] U.S. Cl. ............................................ 600/474; 600/549
[58] Field of Search .................................. 600/474, 549; 128/897; 348/77, 164

[56] References Cited

U.S. PATENT DOCUMENTS

| | | |
|---|---|---|
| Re. 30,446 | 12/1980 | Meyers et al. . |
| 4,175,543 | 11/1979 | Suzuki et al. . |
| 4,215,275 | 7/1980 | Wickersheim . |
| 4,218,707 | 8/1980 | Reed et al. . |
| 4,286,602 | 9/1981 | Guy . |
| 4,327,743 | 5/1982 | Katz . |
| 4,366,381 | 12/1982 | Fischer et al. . |
| 4,428,382 | 1/1984 | Walsall et al. . |
| 4,445,516 | 5/1984 | Wollnik et al. . |
| 4,515,165 | 5/1985 | Carroll . |
| 4,691,712 | 9/1987 | Brown, Jr. . |
| 5,056,525 | 10/1991 | Hafezi . |
| 5,455,157 | 10/1995 | Adachi et al. . |
| 5,603,328 | 2/1997 | Zucker et al. . |
| 5,662,110 | 9/1997 | Carr . |
| 5,779,635 | 7/1998 | Carr . |
| 5,834,661 | 11/1998 | Nonaka et al. . |

Primary Examiner—Marvin M. Lateef
Assistant Examiner—Shawna J. Shaw
Attorney, Agent, or Firm—R. Neil Sudol; Henry D. Coleman

[57] ABSTRACT

A thermographic device has a elongated handle, provided with a small fan (3), and a frame (6) and an image acquisition camera (9) provided at the respective ends of the handle. The frame is provided with a quick coupling (7) for a thermographic plate and the fan is suitable to blow air onto the surface of the organ to be examined before resting the thermographic plate.

10 Claims, 2 Drawing Sheets

THERMOGRAPHIC DEVICE FOR EXAMINING THE BLOOD CIRCULATION

BACKGROUND OF THE INVENTION

1. Field of the invention

The present invention relates to a thermographic device for examining the blood circulation of particular organs, such as for example the breast, the thyroid or others.

2. Description of the Prior Art

The state of the art includes thermographic devices which are constituted by a frame for supporting a heat-sensitive plate (that is to say, a plate whose surface is slightly deformable and changes in color in certain points according to the temperature of the surface against which it is rested) and by a photographic camera with color film for taking photographs of the heat-sensitive plate.

The images that can be obtained with currently commercially available devices often have haloes which are difficult to read and interpret, due to the fact that it is not possible to discriminate whether the thermal situation detected by skin contact is due to superficial blood flow or to deep vessel flow.

In addition to this, the heat signal due to deep circulation diverges as it moves away from the vessel and toward the surface of the body: for example at the regions affected by the large deep vessels of the breasts, currently obtainable thermographic images have large haloes with blurred contours and dimensions which are significantly larger than the actual dimensions of the deep vessels.

It has been found experimentally that the less a thermographic examination is disturbed by the thermal situation due to surface blood flow, the more it improves in significance, reliability and unequivocally of interpretation.

In practice, it has been found that if the surface of the organ to be examined, for example the breasts, is cooled appropriately before resting the thermographic plate, the images that form on the plate are first of all less disturbed by the heat due to surface blood flow and secondly, over time, are affected by the heat that gradually arrives from the deep regions: essentially, it is possible to choose, among the images that appear sequentially, those that are most significant and indicative of the thermal and circulatory situation at the various depths of the organ.

An aim of the present invention is to obviate the above cited drawbacks of conventional devices.

An object of the invention is to provide a thermographic device which allows to produce images which are affected to a limited extent by surface blood circulation and allows to obtain a series of images from which it is possible to clearly detect the situation of functional blood circulation at various depths.

A further object of the present invention is to provided a device constituted by components which are easy to manufacture, procure and assemble, be intuitive and safe in use and effective in operation, and to require limited maintenance.

SUMMARY OF THE INVENTION

The above aims, and other aims that will become apparent to those skilled in the art, are achieved by a thermographic device comprising a handle which supports a small fan and to the respective ends of which a frame and an image acquisition camera are fixed, the frame being provided with a quick-coupling means for a thermographic plate, the fan being suitable to blow air onto the surface of the organ to be analyzed before resting the thermographic plate.

Further characteristics and advantages of the invention will become apparent from a reading of the detailed description of a preferred but not exclusive embodiment of a device. according to the invention, illustrated only by way of a non-limiting example in the accompanying drawings.

DESCRIPTION OF THE PREFERRED EMBODIMENTS OF THE INVENTION

Figure 1:
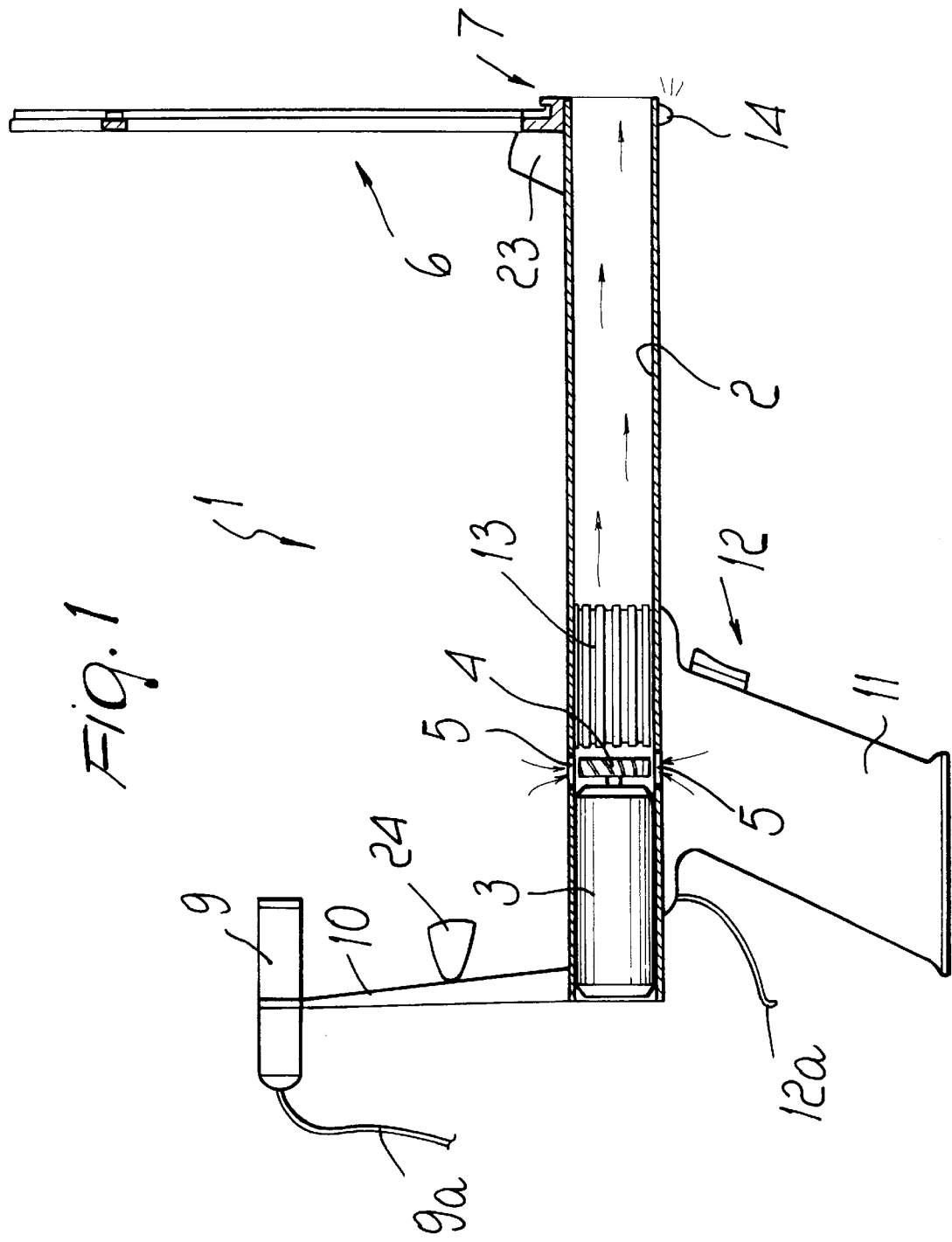
FIG. 1 is a sectional side view, taken along a median plane, of the thermographic device according to the invention.

With particular reference to FIG. 1, the numeral 1 generally designates the thermographic device according to the invention, which includes an elongated handle 2 which is preferably tubular and internally contains a small fan 3. Fan 3 is electrically powered at low voltage and has an impeller 4. The numeral 5 designates holes of the handle for the intake of the air that is blown.

A frame 6 and an image acquisition camera 9 are fixed to the respective ends above the handle 2. Frame 6 is provided with a quick-coupling means 7 for a thermographic plate 8, and the camera 9 can be of any kind but is preferably a videocamera for acquiring color images and adapted to be connected, by means of a cable 9a, to a computer, preferably provided with a printer, or to a videorecorder. Camera 9 is mounted at the top of a support 10, whose base is fixed above the rear region of the handle 2.

Handle 2 is provided, in a downward and substantially rearward region, with a hand grip 11 on which switches 12, connected to the power supply by virtue of a power supply cable 12a, are fitted. The switches control the fan 3 and the camera 9 and can be actuated sequentially: the first one to blow air and cool the surface of the organ to be examined and the second one to record the images that form sequentially on the plate 8 while it is rested and pressed against the surface of the organ. Advantageously, a single three-position switch 12 can be installed on the handle, one of the positions being a stable power-off position.

An air stream cooling device 13 is associated in front of the fan 9 and can be of any kind but is conveniently an electrically-powered heat exchanger, preferably of the type that uses the Peltier effect of bimetallic conductors. The cooling device 13 can be activated simultaneously with the fan 9 or can have a separate activation switch.

To assist or replace the cooling device 13, in front of the handle 2 it is possible to fit a nozzle 14 for atomizing suitable fluids. Nozzle 14 is adapted to spray a few drops of liquid, in the form of very fine droplets, onto the surface to be examined in order to enhance the cooling effect produced by the fan. Nozzle 14 can be actuated by a small manual or electric pump.

Figure 2:
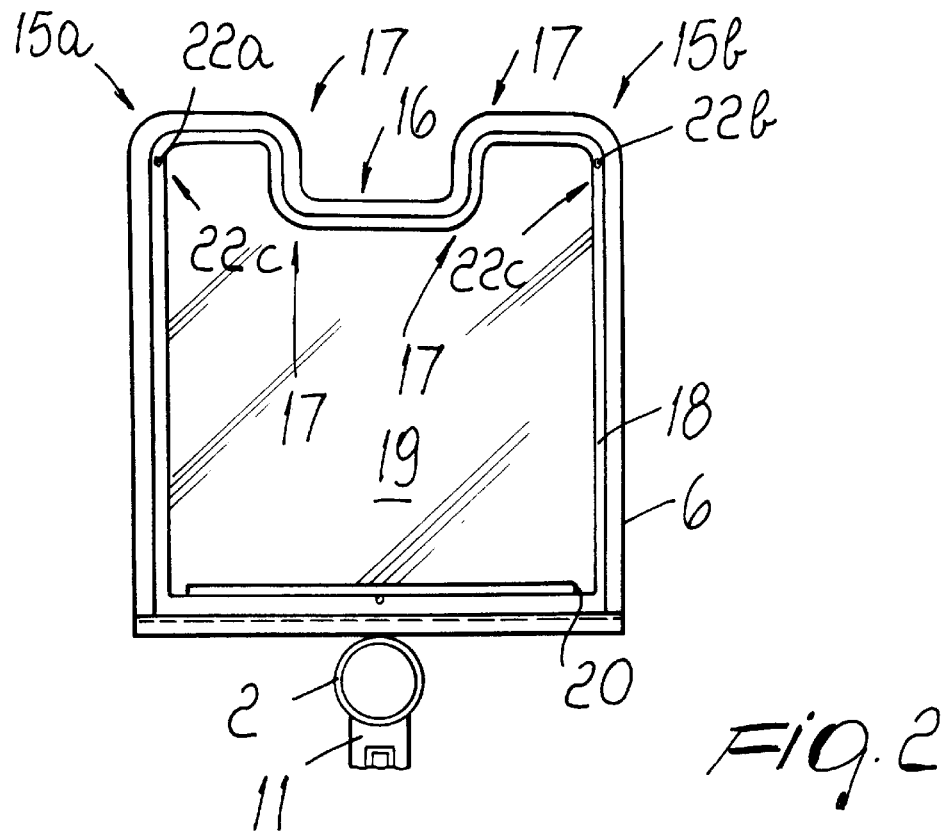
FIG. 2 is a front view of the device.
Figure 3:
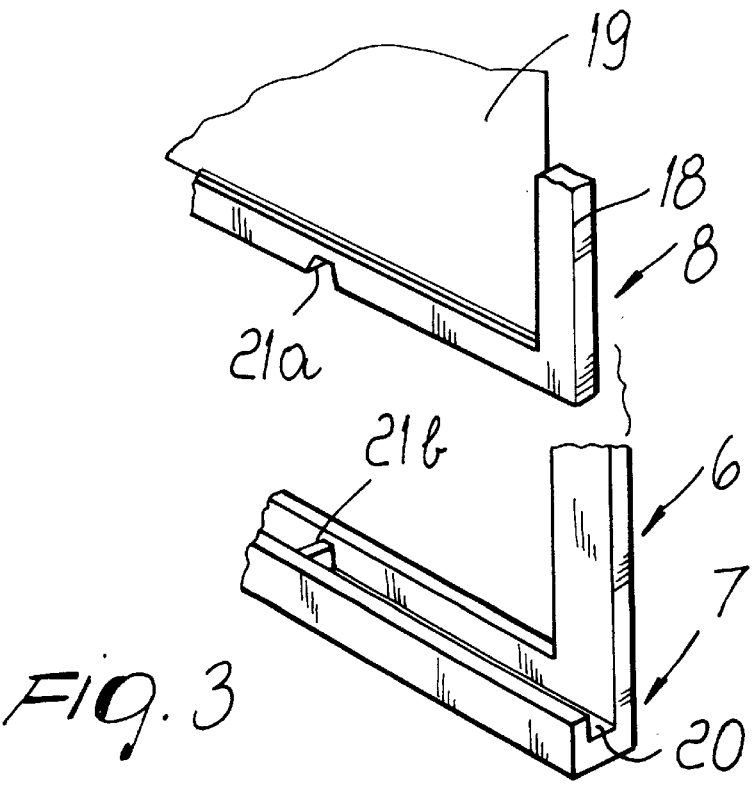
FIG. 3 is an exploded perspective view of a detail of the means for coupling the frame to the thermographic plate.

The frame 6 and the thermographic plate 8, shown in particular in FIGS. 2 and 3, are preferably rectangular and the upper edge has rounded corners 15a and 15b and is centrally affected by a recess 16 with equally rounded corners 17. The profile of the upper edge of the frame and of the plate allow to examine body regions located beyond the breast, that is to say, the axillary fossa in case of breast examination.

The thermographic plate 8 is constituted by a substantially rigid perimetric border 18 in which a thin blade 19, made of flexible material, such as a cellophane film or a material known by the trade-name Mylar, is stretched. A layer of black paint and a few successive layers of a liquid-crystal solution are applied to the film, and thermographic plates are advantageously prepared which have different temperature sensitivities and can be used selectively according to the working requirements. The means 7 for the quick coupling of the plate 8 to the frame 6 includes, in the present example, a lower drip rail 20 which is open upward and is arranged in front of the frame 6 on which the lower side of the plate can be locked. In order to center the plate with respect to the frame, the border of the plate has a central notch 21a, at its lower side. Central notch 21a is adapted to cooperate with a corresponding central tab 21b of the drip rail 20. At least one permanent magnet, two magnets 22a and 22b in this particular example, are mounted in the upper part of the frame and are adapted to rigidly couple respective ferromagnetic buttons 22c which are rigidly coupled to the perimetric border of the plate.

A luminous display 23 is located at the base of the frame 6 and is directed toward the rear and displays, for example by acting on the keyboard of the computer, a patient identification code, the date or other information. If necessary, an additional light source 24 for the display 23 can be installed proximate to the camera.

It has been found that the thermographic device according to the invention allows, by acting with just one hand and with a single instrument, to first cool the surface of the organ to be examined and then to rest and press the thermographic plate against the skin. Changes in the color images appear on the surface of the plate in relation to the temperature reached by the skin, and it is possible to acquire and store in succession the images that progressively form. The first recorded images are not influenced by heat produced by surface circulation and are accordingly certainly sharper and easier to interpret and to attribute to gradually deeper blood circulation than images that can be obtained with conventional equipment.

The device according to the invention is susceptible to numerous modifications and variations, all of which are within the scope of the inventive concept as defined by the appended claims. All the details may furthermore be replaced with other technically equivalent elements.

In practice, the materials employed, as well as the dimensions, may be any according to the requirements.

I claim:

1. A thermographic device for examining organs, comprising:

a handle supporting a fan; and a frame and an image acquisition camera associated with respective ends of said handle, said frame being provided with a quick-coupling means for a thermographic plate, said fan being adapted to blow air onto the surface of an organ to be examined before resting the thermographic plate on said organ, wherein said handle is hollow and said face is mounted inside said handle.

2. The thermographic device according to claim 1, wherein said handle has, in a downward region and to the rear, a hand grip having switches connected to a power supply of said fan and of said camera and adapted to be actuated in succession.

3. The thermographic device according to claim 1, wherein a device for cooling the generated air stream is associated with said fan.

4. The thermographic device according to claim 3, wherein said cooling device includes of bimetallic conductors.

5. The thermographic device according to claim 1, wherein an atomizer is mounted at a front end of said handle and is suitable to spray droplets onto the surface to be examined in order to increase the cooling effect of the fan.

6. The thermographic device according to claim 1, wherein a luminous display is provided at the base of said frame for displaying patient identification data, the date or other information.

7. The thermographic device according to claim 1, wherein said quick-coupling means of the frame comprises a lower drip rail which is open upward, is arranged in front of the frame and is suitable for resting the lower side of said thermographic plate.

8. The thermographic device according to claim 1, wherein said frame quick-coupling means comprises at least one permanent magnet which is arranged in the upper part of the frame and is suitable to rigidly couple a ferromagnetic button which is rigidly associated with the plate.

9. The thermographic device according to claim 1, wherein said frame and said thermographic plate are substantially rectangular and their upper edge has rounded corners and is centrally provided with a recess having rounded corners.

10. The thermographic device according to claim 1, wherein said image acquisition camera is a television camera.

* * * * *